(12) United States Patent
Makovec et al.

(10) Patent No.: US 7,202,277 B2
(45) Date of Patent: Apr. 10, 2007

(54) BENZAMIDINE DERIVATIVES HAVING ANTI-INFLAMMATORY AND IMMUNOSUPPRESSIVE ACTIVITY

(75) Inventors: Francesco Makovec, Monza (IT); Simona Zanzola, Milan (IT); Roberto Artusi, Rho (IT); Lucio Claudio Rovati, Monza (IT)

(73) Assignee: Rotta Research Laboratorium S.p.A., Milan (IT)

( * ) Notice: Subject to any disclaimer, the term of this patent is extended or adjusted under 35 U.S.C. 154(b) by 0 days.

(21) Appl. No.: 10/467,624

(22) PCT Filed: Feb. 6, 2002

(86) PCT No.: PCT/EP02/01201

§ 371 (c)(1),
(2), (4) Date: Jan. 6, 2004

(87) PCT Pub. No.: WO02/070468

PCT Pub. Date: Sep. 12, 2002

(65) Prior Publication Data

US 2004/0110801 A1     Jun. 10, 2004

(30) Foreign Application Priority Data

Feb. 8, 2001  (IT) ............... TO01A0110

(51) Int. Cl.
*A61K 31/17* (2006.01)
(52) U.S. Cl. .......... 514/596; 514/585; 514/623; 514/625; 514/419
(58) Field of Classification Search ............ 564/26, 564/27, 48, 188, 189, 218; 514/585, 596, 514/623, 625, 419; 548/491
See application file for complete search history.

(56) References Cited

U.S. PATENT DOCUMENTS

| | | | | |
|---|---|---|---|---|
| 2,559,085 | A | * 7/1951 | McKay | 564/108 |
| 4,024,183 | A | * 5/1977 | Swallow | 564/51 |
| 5,240,694 | A | * 8/1993 | Gwaltney, Jr. | 424/45 |

FOREIGN PATENT DOCUMENTS

| | | | |
|---|---|---|---|
| DE | 950637 | * | 10/1956 |
| FR | 2 456 731 | A | 12/1980 |
| WO | WO 91/04024 | | 4/1991 |
| WO | WO 93/13055 | | 7/1993 |
| WO | WO 95/00505 | | 1/1995 |
| WO | WO 97 08145 | A | 3/1997 |
| WO | WO 97 36859 | A | 10/1997 |
| WO | WO 97 36862 | A | 10/1997 |
| WO | WO 01 44172 | A | 6/2001 |

OTHER PUBLICATIONS

Swallow et al, Annals New York Academy of Sciences, vol. 284, pp. 305-309, 1977.*
George Cy Chiou et al.; Exp. Opin. Ther. Patents (1996), vol. 6(1), pp. 41-56, Ashley Publications Ltd. ISSN 1354-3776.
James B Summers et al.; Annual Reports in Med. Chemistry vol. 33, pp. 131-140, Academic Press 1998.

* cited by examiner

*Primary Examiner*—Shailendra Kumar
(74) *Attorney, Agent, or Firm*—Sughrue Mion, PLLC

(57) ABSTRACT

Compounds which can be represented by the general formula (I) indicated below:

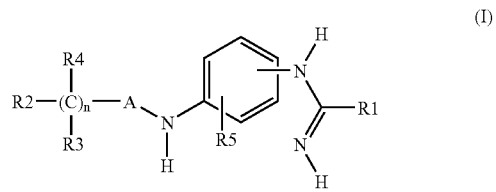

(I)

and in which:
A is selected independently from the carboxamide group, the thiocarboxamide group, and the carbonyl group,
$R_1$ is selected from an alkyl group having from 1 to 3 carbon atoms and the amino group, unsubstituted or substituted with the nitro group or the methyl group,
$R_2$ is selected independently from hydrogen, an alkyl group having from 1 to 4 carbon atoms, the methoxy, ethoxy, propoxy group, a mono-, bi- or tricyclic cycloalkane residue having from 5 to 12 carbon atoms, the adamantyl group, an aryl, naphthyl or heterocyclic group, unsubstituted or substituted with methyl, methoxy, hydroxy, amino or halogen groups,
$R_3$ and $R_4$ are selected independently from hydrogen and an alkyl group having from 1 to 3 carbon atoms,
$R_5$ represents one or two substituents independently selected from hydrogen and the methyl, methoxyl and hydroxyl groups,
n is a whole number from 0 to 6, and
the amidine group is in the para or meta position relative to the "-A-NH—" group.

2 Claims, No Drawings

BENZAMIDINE DERIVATIVES HAVING ANTI-INFLAMMATORY AND IMMUNOSUPPRESSIVE ACTIVITY

This is a National Stage Entry of Application No. PCT/EP02/01201 filed Feb. 6, 2002, the disclosure of which is incorporated herein by reference.

BACKGROUND OF THE INVENTION

The subject of the present invention is novel amidine derivatives of phenylenediamine which can be represented by the general formula (I) indicated below:

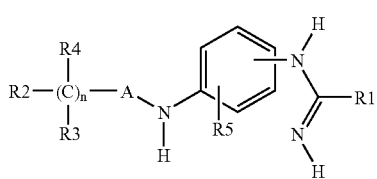

and in which:
- A is selected independently from the carboxamide group, the thiocarboxamide group, and the carbonyl group,
- $R_1$ is selected from an alkyl group having from 1 to 3 carbon atoms and the amino group, unsubstituted or substituted with the nitro group or the methyl group,
- $R_2$ is selected independently from hydrogen, an alkyl group having from 1 to 4 carbon atoms, the methoxy, ethoxy, or propoxy group, a mono-, bi- or tricyclic cycloalkane residue having from 5 to 12 carbon atoms, the adamantyl group, an aryl, naphthyl or heterocyclic group, unsubstituted or substituted with methyl, methoxy, hydroxy, amino or halogen groups,
- $R_3$ and $R_4$ are selected independently from hydrogen and an alkyl group having from 1 to 3 carbon atoms,
- $R_5$ represents one or two substituents independently selected from hydrogen and the methyl, methoxyl and hydroxyl groups,
- n is a whole number from 0 to 6, and
- the amidine group is in the para or meta position relative to the "-A-NH—" group.

In the compounds of the invention, $R_2$ is directly linked to the A group (n=o) or is linked to A through an alkylene group, having from 1 to 6 carbon atoms, optionally substituted with one or more alkyl groups having from 1 to 3 carbon atoms.

SUMMARY OF THE INVENTION

The compounds of the present invention have been found to be potent antagonists of various mediators of inflammation and also have immunosuppressive properties. In vitro, they have been found to be inhibitors of inducible nitric oxide synthase (iNOS) and of the enzyme cyclooxygenase (COX). In vivo, they have been found to be potent inhibitors of the cytokine "tumour necrosis factor" (TNFα). Moreover, many of the products of the invention can antagonise the collagenase activity of the metalloproteases.

Nitric oxide (NO) is formed at cell level by L-arginine, by means of the enzyme NOS. There are three subtypes of this enzyme. The enzyme (iNOS) which can be induced in the presence of pro-inflammatory cytokines or of endotoxins is expressed in cells of many types, amongst which are macrophages and neutrophiles.

Vasodilatation, which is a characteristic of acute inflammation, depends, for many mediators of the inflammatory process, such as, for example, histamine, bradykinin, substance P, PAF, etc., on the release of NO. In general, NO increases the inflammatory responses in many experimental models, both acute and chronic.

It should be noted that NO can be produced massively in response to a stimulus induced by cytokines in the inflamed joints of patients with rheumatoid arthritis and osteoarthritis, and that the plasma concentrations of NO in the sinovial fluid in these patients are generally very high.

The fact that the activity of iNOS is also very high in the colons of patients with ulcerative colitis is also interesting.

The prostaglandines (PGE) are mediators of inflammation generated by the enzyme cyclooxygenase (COX). The inducible isoform (COX-2) is overproduced ("upregulated") in the inflamed tissues and this leads to increased synthesis of PGE.

There are interactions between the NOS and COX systems and the role of NO in inflammation may therefore depend not only on its direct effect, but also on its modulatory effect on the bio-synthesis of PGE.

TNFα is a primary cytokine which initiates the cascade of events that characterise an inflammatory process, inducing the synthesis and release of secondary cytokines and enzymes such as metalloproteases (MMP, amongst which is collagenase), iNOS and COX-2. As already mentioned, the intestinal mucosa is one of the most important sites of pro-inflammatory cytokine production, as observed in pathological conditions such as chronic inflammation of the colon (IBS) and ulcerative colitis.

It can therefore be considered that the compounds of the present invention may be used with advantage in the treatment of various diseases in man which are characterised by non-specific inflammation such as, for example, rheumatoid arthritis which is a syndrome with a chronic course which can develop into progressive destruction of the joint and periarticular structures, osteoarthrosis which is a disease characterised by the degeneration of the joint cartilage, often accompanied by secondary inflammation of the sinovial membrane, or in other pathological conditions, for example, in the gastrointestinal system, ulcerative colitis, Crohn's disease, IBS or food allergies and intolerance.

Advantageous use of the compounds of the invention can also be predicted in other areas and systems, for example, in the treatment of pathological conditions of the cardiovascular system with an inflammatory or atherosclerotic basis which are sensitive to treatment of iNOS inhibitors.

Moreover, for the compounds of the invention which have MMP-inhibiting activity, advantageous use can be predicted in the treatment of tumoral conditions, since they potentially prevent localised or metastatic invasion of tumoral cells, both by inhibiting the activation of various growth factors and by blocking angiogenesis.

An enormous number of studies have been performed in the search for drugs with anti-inflammatory activity which can perform an inhibiting action on pro-inflammatory cytokines and which are free of the side effects of conventional antiinflammatory drugs (COX inhibitors).

Chiou et al [Exp. Opin, Ther. Patents 6(1), 41–56 (1996)] have recently reviewed, in a monographic work, a large number of publications and patents in which various classes of compounds which inhibit the production of cytokines by blocking their release, their receptors, or their converting enzymes, are described. Many monographic works have also been published on the inhibitors of MMPs, such as, for example, that of Summers et al [Annual Reports in Med. Chemistry 33, 131–140 (1998)] in which various chemical classes of MMP inhibitors are examined and their therapeutic potential is discussed. Amongst others, patents in which the NO-synthase inhibitory activity of various amidines is described, such as, for example, the patent PCT/GB/92/02387 and the patent PCT/GB/94/01325, have been published.

However, the compounds described are amidine derivatives of amino-acids which are structurally very similar to analogous derivatives of L-arginine, such as L-N-monomethyl arginine which is the subject of the patent WO91/04024, but are different from the benzamidines of the present invention, both structurally and with regard to their pharmacological activity as a whole.

All of these publications and researches show that there is a great therapeutic need to find ever more potent and better-tolerated novel anti-inflammatory drugs. In accordance with this need, the object of the present invention is to provide, for treatment, novel drugs which, simultaneously, have anti-inflammatory and immunosuppressive activity, expressed by their combined iNOS and COX antagonistic activities, their MMP-inhibiting activity, and their activity in inhibiting the production of TNF-α, and which can thus be used advantageously in the treatment of pathological conditions in man which are characterised by non-specific or autoimmune-based inflammation.

Pharmaceutical forms of the compounds of the invention can be prepared by conventional techniques, for example, as tablets, pills, capsules, suppositories, suspensions, solutions, patches, creams or ointments, and can be administered by oral, parenteral, rectal, transdermal, or transmucosal routes, or in other forms suitable for achieving the therapeutic effect such as, for example, solid preparations for oral use with delayed action which permit the controlled release of the active substance over time.

The active ingredient is usually administered to the patient with a reference dose variable from 0.1 to 10 mg/kg of body weight per dose.

For parenteral administration, the use of a water-soluble salt of the compounds of the invention such as the hydrochloride or another salt derived from a non-toxic and pharmaceutically-acceptable inorganic or organic acid is preferred. For the derivatives of the invention with a slightly acid character, such as the derivatives in which $R_1$ is the nitro-amino group, the corresponding sodium salts or equivalent salts can be prepared by conventional methods.

Substances commonly used in pharmaceuticals such as excipients, binders, flavourings, disaggregants, substances for stimulating transdermal and transmucosal absorption, colourings, humectants, etc., may be used as inactive ingredients.

The method for the preparation of the derivatives of the invention consists of a series of reactions which comprises:

a) reacting the 1, 3 or 1,4-phenylenediamine of formula (IV), suitably substituted and in which $R_5$ has the meaning given above, with the appropriate isothiocyanate (V A), acyl chloride (V B), or isocyanate (V C), in which $R_2$, $R_3$, $R_4$ and n have the meanings given above, in the presence of an excess of phenylenediamine, in an inert solvent and at a temperature of between 4° C. and the reflux temperature of the solvent used, to give the corresponding anilines of formula (III) in which $R_2$, $R_3$, $R_4$, $R_5$, A and n have the meanings given above, and in which the amine group is in the meta or para position relative to the chain with the "A-NH" group (see General Synthesis Scheme, Step 1), and b) reacting the anilines of formula (III), in which $R_2$, $R_3$, $R_4$, $R_5$, A and n have the meanings given above, with the appropriate imidate of formula II, generally salified in hydrochloride form, in which $R_1$ has the meaning given above.

The reaction takes place in the presence of an excess of (II) relative to (III) (preferably of 2 moles to 1) and in the presence of a stoichiometric quantity, relative to (II), of a tertiary base, preferably triethylamine, in an inert anhydrous solvent, such as, for example tetrahydrofuran, at a temperature of between 4° C. and the boiling point of the solvent, for a period of between 2 and 48 hours, to give the corresponding final derivatives of formula (I) in which A, $R_1$, $R_2$, $R_3$, $R_4$, $R_5$ and n have the meanings given above and in which the amidine group is in the para or meta position relative to the "A-NH" group.

The compounds of formula (I) described in Table 2 (I-30 and I-31) were obtained with the use of reagents other than those of the general formula (II) and, in particular, benzotriazolo-1-carboxamidinium tosylate (see Example 5) and N-methyl-N-nitroso-N'-nitroguanidine (see Example 6), respectively.

The starting phenylenediamines, as well as the isothiocyanates (V A), the acyl chlorides (V B), the isocyanates (V C), and the imidates of formula (II) are commercially available or were prepared by conventional methods in accordance with existing literature.

General Synthesis Scheme (Scheme 1)

Step 1

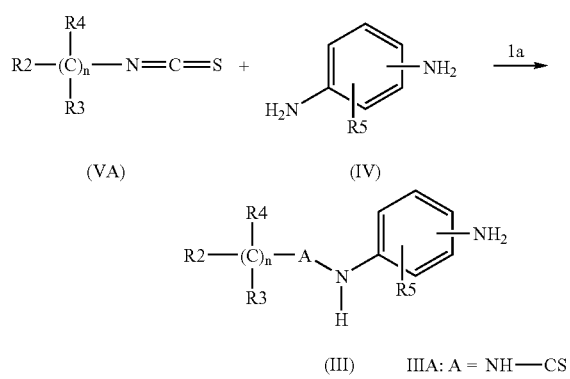

-continued

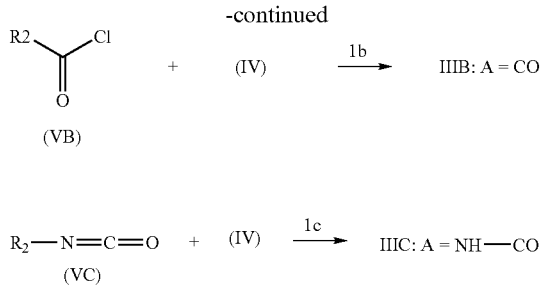

Step 2

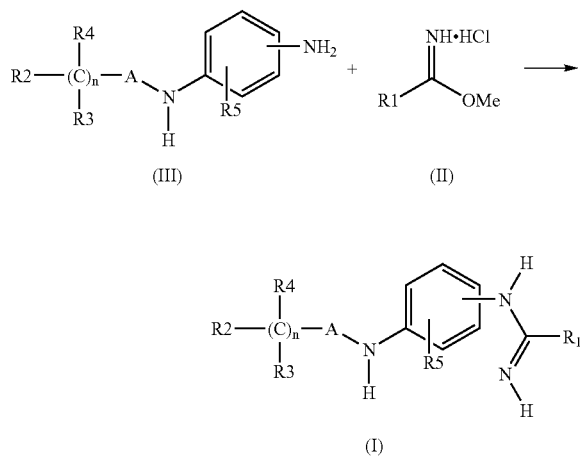

The following examples are given below as further illustration of the invention.

EXAMPLE 1

Preparation of N-(4-aminophenyl)-N'-pentyl thiourea (Compound III-4 of Table 1).

71.8 g of 1,4-phenylenediamine (0.66 moles) was suspended in 300 ml of tetrahydrofuran, and 43 g of pentyl isothiocyanate (0.33 moles), dissolved in 50 ml of tetrahydrofuran, was added slowly dropwise, with stirring and at ambient temperature. After 24 hours, the solvent was evaporated under vacuum and the residue, taken up with ethyl acetate, was washed with water, 0.1N citric acid, saturated sodium bicarbonate, and water to neutral pH. The solvent was rendered anhydrous with anhydrous sodium sulphate and evaporated under vacuum, to give 75 g of crude product which was re-crystallised from toluene. 60 g was obtained.

Formula: $C_{12}H_{19}N_3S$ (M.W. 237.46). Yield 77%.

TLC: (chloroform/methanol 9/1) rf 0.7. M.P. 125° C.

HPLC: retention time (rt) 4.60 minutes.

HPLC conditions: Supelcosil LC-DP column, 100×4.6 mm, eluent $KH_2PO_4$ 0.01M 25/MetOH 27/MetCN 48 (pH 2.1), flow 0.4 ml/min, UV detector at 248 nm.

$^1$HNMR (DMSO-$d_6$), ppm: 2.21 (bt, 3H, J=5.60 Hz); 0.98–1.71 (m, 6H); 3.33 (q, 2H, J=6.68 Hz); 4.93 (bs, 2H); 6.45 (d, 2H, J=8.59 Hz); 6.81 (d, 2H, J=8.59 Hz); 7.05 (m, 1H); 8.88 (s, 1H).

All of the intermediate compounds of formula (III) according to the invention in which A is the thiocarboxamide group were synthesised with the use of the same method (see Scheme 1, step 1a).

EXAMPLE 2

Preparation of N-(4-aminophenyl)-N'-pentylamide (Compound III-22 of Table 1).

20.2 g di 1,4-phenylenediamine (0.181 moles) was dissolved in 200 ml of tetrahydrofuran, together with 11.1 ml of triethylamine (0.080 moles). The solution was cooled to 0° C. and 10 ml of caproyl chloride (0.0724 moles) was added slowly dropwise so that the temperature did not exceed 5° C. Upon completion of the addition, the temperature was increased to ambient temperature. After reaction for 24 hours, the solvent was evaporated under vacuum and the residue, taken up with ethyl acetate, was washed with water. The solvent was rendered anhydrous with anhydrous sodium sulphate and evaporated under vacuum to give 12 g of crude product which was re-crystallised from toluene. 7.5 g was obtained.

Formula: $C_{12}H_{18}N_2O$ (M.W. 206.28). Yield 51%

TLC: (chloroform/methanol 9/1) rf 0.51. M.P. 88.5–89° C.

HPLC: retention time (rt) 5.54 minutes.

HPLC conditions: see Example 1.

$^1$HNMR (DMSO-$d_6$), ppm: 0.86 (bt, 3H, J=5.59 Hz); 1.03–1.79 (m, 6H); 2.18 (t, 2H, J=6.99 Hz); 4.69 (s, 2H); 6.43 (d, 2H, J=8.39 Hz); 7.15 (d, 2H, J=8.39 Hz); 9.28 (s, 1H).

EXAMPLE 3

Preparation of N-(4-aminophenyl)-N'-cyclohexyl urea (Compound III-28 of Table 1).

10.4 g of 1,4-phenylenediamine (0.095 moles) was suspended in 100 ml of tetrahydrofuran and 5 ml of cyclohexyl isocyanate (0.038 moles), dissolved in 20 ml of tetrahydrofuran, was added slowly dropwise, with stirring and at ambient temperature. After 24 hours, the solid formed was filtered out and washed with cold tetrahydrofuran, water, and ethyl ether. 8.8 g was obtained.

Formula: $C_{13}H_{19}N_3O$ (M.W. 233.31). Yield 98%

TLC: (chloroform/methanol 9/1) rf 0.40. M.P. 199.8–202.4° C.

HPLC: retention time (rt) 6.39 minutes.

HPLC conditions: see Example 1.

$^1$HNMR (DMSO-$d_6$), ppm: 0.75–2.00 (m, 10H); 3.47 (m, 1H); 4.62 (bs, 2H); 5.75 (d, 2H, J=7.50 Hz); 6.49 (d, 2H, J=8.75 Hz); 7.00 (d, 2H, J=8.75 Hz); 7.75 (bs, 1H).

Some derivatives of formula (III) obtained as described above are given in Table 1 below, with some identifying chemical and physical characteristics.

TABLE 1

Compounds of formula (III)

(III)

$$R_2-(C)_n-A-\underset{H}{N}-\text{Ar}(R_5)-NH_2$$
with $R_4$ and $R_3$ on the carbon.

| Compound | $R_2$ | $R_3$ | n | A | Crude Formula | M.P. (crystallisation solvent)$^d$ | TLC ($R_f$)$^e$ |
|---|---|---|---|---|---|---|---|
| III-1 | $CH_3$ | — | 0 | NH—CS | $C_8H_{11}N_3S$ | 173.5–174.2 (A) | 0.65 (I) |
| III-2 | $CH_3$ | H | 2 | NH—CS | $C_{10}H_{15}N_3S$ | 118.6–120.2 | 0.58 (I) |
| III-3 | $CH_3$ | H | 3 | NH—CS | $C_{11}H_{17}N_3S$ | 124.5–127 | 0.67 (I) |
| III-4 | $CH_3$ | H | 4 | NH—CS | $C_{12}H_{19}N_3S$ | 113–115 (B) | 0.70 (I) |
| III-5 | $CH_3$ | H | 5 | NH—CS | $C_{13}H_{21}N_3S$ | 119.5–120.3 | 0.75 (I) |
| III-6 | $CH_3$ | H | 6 | NH—CS | $C_{14}H_{23}N_3S$ | 107.0–107.4 | 0.75 (I) |
| III-7 | Isopropyl | H | 2 | NH—CS | $C_{12}H_{19}N_3S$ | 153.5–154.6 (B) | 0.60 (I) |
| III-8 | $CH_3$ | $CH_3$ | 1 | NH—CS | $C_{10}H_{15}N_3S$ | 137.2–137.8 (B) | 0.63 (I) |
| III-9 | Ethyl | $CH_3$ | 1 | NH—CS | $C_{12}H_{19}N_3S$ | 165.6–166.8 | 0.75 (I) |
| III-10 | $CH_3$—O | H | 3 | NH—CS | $C_{11}H_{17}N_3OS$ | 104.6–105.2 | 0.65 (I) |
| III-11 | Cyclohexyl | — | 0 | NH—CS | $C_{13}H_{19}N_3S$ | 168.6–169.4 | 0.70 (I) |
| III-12 | Phenyl | — | 0 | NH—CS | $C_{13}H_{13}N_3S$ | 263.0–264.0 (A) | 0.79 (II) |
| III-13 | Phenyl | H | 2 | NH—CS | $C_{15}H_{17}N_3S$ | 168.2–169.0 | 0.83 (II) |
| III-14 | Phenyl | H | 3 | NH—CS | $C_{16}H_{19}N_3S$ | 117.3–117.9 | 0.83 (II) |
| III-15 | 4-F-Phenyl | H | 2 | NH—CS | $C_{15}H_{17}ClFN_3S$ | 190.2–191.6 | 0.85 (II) |
| III-16 | 4-Cl-Phenyl | H | 2 | NH—CS | $C_{15}H_{16}ClN_3S$ | 116.6–116.7 | 0.83 (II) |
| III-17 | 2,6-diF-Phenyl | H | 2 | NH—CS | $C_{15}H_{15}F_2N_3S$ | 147.7–149.7 | 0.50 (I) |
| III-18 | 2-Piridyl | H | 1 | NH—CS | $C_{13}H_{14}N_4S$ | 106.0–108.0 | 0.41 (I) |
| III-19 | 2-Piridyl | H | 2 | NH—CS | $C_{14}H_{16}N_4S$ | 82.0–84.0 | 0.38 (I) |
| III-20 | 5-$CH_3$-2-Thiazolyl | — | 0 | NH—CS | $C_{11}H_{12}N_4S_2$ | 157.5–159.0 | 0.40 (I) |
| III-21 | $CH_3$ | H | 4 | NH—CS | $C_{14}H_{23}N_3S$ | 101.4–102.8 | 0.75 (I) |
| III-22 | $CH_3$ | H | 4 | CO | $C_{12}H_{18}N_2O$ | 88.5–89.0 (B) | 0.51 (I) |
| III-23 | Cyclohexyl | — | 0 | CO | $C_{13}H_{18}N_2O$ | 176.1–177.0 (B) | 0.50 (I) |
| III-24 | 1-Adamantyl | — | 0 | CO | $C_{17}H_{22}N_2O$ | 169.6–171.2 | 0.45 (I) |
| III-25 | 2-Indolyl | — | 0 | CO | $C_{15}H_{13}N_3O$ | 193.8–194.9 (A) | 0.47 (I) |
| III-26 | 3-Indolyl | H | 1 | CO | $C_{16}H_{14}N_3O$ | 122.0–122.7 (B) | 0.40 (I) |
| III-27 | 1-$CH_3$-2-Indolyl | — | 0 | CO | $C_{16}H_{15}N_3O$ | 232.6–235.3 | 0.55 (I) |
| III-28 | Cyclohexyl | — | 0 | NH—CO | $C_{13}H_{19}N_3O$ | 199.8–202.4 | 0.40 (I) |
| III-29 | Cyclohexyl | — | 0 | NH—CS | $C_{13}H_{19}N_3S$ | 101.0–102.8 | 0.70 (I) |

Note:
a) In all of the compounds given by way of example, $R_4$ is H, with the exception of compound III-9 in which $R_4$ is $CH_3$.
b) In all of the compounds given by way of example, the amino group is in the para position relative to the "NH-A" group, with the exception of compound III-29 in which the amino group is in the meta position relative to the "NH-A" group.
c) In all of the compounds given by way of example, $R_5$ is H except for compound III-21 in which $R_5$ is 2,5-dimethyl.
$^d$Crystallisation solvent: A (isopropanol); B (toluene).
$^e$Eluent: (I) chloroform/methanol (9/1) (v/v); (II) chloroform/methanol/water/ammonia (85/25/2/1) (v/v).

EXAMPLE 4

Preparation of N-[4-(N-acetamidine)phenyl]-N'-pentyl thiourea (Compound I-4 of Table 2).

55 g di N-(4-aminophenyl)-N'-pentyl thiourea (0.23 moles) was dissolved in 300 ml of tetrahydrofuran. 64.5 ml of triethylamine (0.46 moles) and 50.7 g of methyl acetimidate hydrochloride (0.46 moles) was added, with stirring at ambient temperature; the pH of the suspension was approximately 9. After 24 hours (the pH fell to 7), the solid was filtered out and washed with a little tetrahydrofuran and ethyl ether. The residue, taken up with water, was rendered basic with 4N sodium hydroxide to pH 11 and was left for 1 hour with stirring and then filtered, washed with water, and ethyl ether and purified hot with acetonitrile. 51 g was obtained.

Formula: $C_{14}H_{22}N_4S$ (M.W. 278.42). Yield 80%.

TLC: (butanol/acetic acid/water 5/2/2) rf 0.70; (chloroform/methanol saturated with ammonia 9/1) rf 0.37. M.P. 191.4° C.

HPLC: retention time (rt) 7.70 minutes.

HPLC conditions: see Example 1.

$^1$HNMR (DMSO-$d_6$), ppm: 0.88 (bt, 3H, J=5.60 Hz); 1.00–1.55 (m, 6H); 1.82 (s, 3H); 3.35 (m, 2H); 5.91 (bs, 1H); 6.63 (d, 2H, J=8.56 Hz); 7.11 (d, 2H, J=8.56 Hz); 7.28 (bs, 1H); 9.08 (bs, 1H).

All of the derivatives of formula (I) in which R1 was methyl were prepared in similar manner with the use of the appropriate aniline of formula (III) in place of N-(4-aminophenyl)-N'-pentyl thiourea.

EXAMPLE 5

Preparation of 1-guanidinophenyl-4-cyclohexyl thiourea (Compound I-30 of Table 2).

15 g of N-(4-aminophenyl)-N'-cyclohexyl thiourea (0.06 moles) was suspended in 100 ml of acetonitrile, and 20 g of benzotriazolo-1-carboxamidinium tosylate [0.06 moles, Katrizky, A. R. et al. Synth. Comm. 25(8), 1173–1186, (1995)] was added, with stirring at ambient temperature. After 72 hours, the solvent was evaporated under vacuum and the residue, taken up with ethyl acetate, was washed with 0.1N sodium hydroxide and extracted with 0.1N citric acid. The aqueous phase was brought to pH 9 with 2N sodium hydroxide, and extracted with ethyl acetate and the organic phase was washed with water. The solvent was rendered anhydrous over anhydrous sodium sulphate and evaporated under vacuum to give 8 g of crude product which was purified with isopropyl ether. 7.4 g was obtained.

Formula: $C_{14}H_{21}N_5S$ (M.W. 291.42). Yield 43%.

TLC: (butanol/acetic acid/water 5/2/2) rf 0.71. M.P. 188.6° C.

HPLC: retention time (rt) 8.0 minutes.

HPLC conditions: see Example 1. $^1$HNMR (DMSO-$d_6$), ppm: 0.67–2.17 (m, 10H); 4.05 (m, 1H); 5.73 (bm, 6H); 6.71 (d, 2H, J=8.43 Hz); 7.17 (d, 2H, J=8.43 Hz).

EXAMPLE 6

Preparation of 1-nitroguanidinophenyl-4-cyclohexyl thiourea (Compound I-31 of Table 2).

9 g of N-(4-aminophenyl)-N'-cyclohexyl thiourea (0.036 moles) was suspended in 140 ml of a 1/1 ethanol/water mixture, and 3 g of N-methyl-N-nitroso-N'-nitroguanidine [0.021 moles, McKay, A. F. J. Am. Chem. Soc. 71, 1968–1970,(1949)] was added, with stirring at ambient temperature. After 2 hours at ambient temperature, the reaction mixture was heated under reflux for 1 hour; the precipitate which formed was filtered hot, washed with ethyl ether and dried. 3.8 g was obtained.

Formula: $C_{14}H_{20}N_6O_2S$ (M.W. 336.41). Yield 54%.

TLC: (butanol/acetic acid/water 5/2/2) rf 0.95. M.P. 215.2° C.

HPLC: retention time (rt) 4.16 minutes.

HPLC conditions: see Example 1.

$^1$HNMR (DMSO-$d_6$), ppm: 0.84–1.99 (m, 10H); 4.01 (m, 1H); 7.15 (d, 2H, J=8.76 Hz); 7.42 (d, 2H, J=8.76 Hz); 7.52 (bd, 1H, J=7.64 Hz); 8.03 (bs, 2H); 9.28 (s, 1H); 9.42 (bs, 1H).

EXAMPLE 7

Preparation of N-[4-(N-acetamidino)phenyl]-N'-pentyl thiourea hydrochloride (the hydrochloride of Compound I-4).

3 g of N-[4-(N-acetamidino)phenyl]-N'-pentyl thiourea (0.011 moles) was dissolved in 1N HCl. After 0.5 hours at ambient temperature, the precipitate which formed was filtered out, washed with a little water, and with ethyl ether, and dried. 3.2 g was obtained.

Formula: $C_{14}H_{23}ClN_4S$ (M.W. 314.88). Yield 93%.

TLC: (butanol/acetic acid/water 5/2/2) rf 0.70. M.P. 180.6° C.

$^1$HNMR (DMSO-$d_6$), ppm: 0.84 (t, 3H, J=5.60 Hz); 1.02–1.78 (m, 6H); 2.28 (s, 3H); 3.43 (bq, 2H, J=6.05 Hz); 7.15 (d, 2H, J=8.56 Hz); 7.73 (d, 2H, J=8.56 Hz); 8.39 (m, 1H); 9.42 (bs, 1H); 10.38 (s, 1H); 11.28 (s, 1H).

Some derivatives of formula (I) obtained according to the invention are given in Table 2 below, with some identifying, chemical and physical characteristics, without thereby in any way limiting the spirit or the scope of the invention.

TABLE 2

Compounds of formula (I)

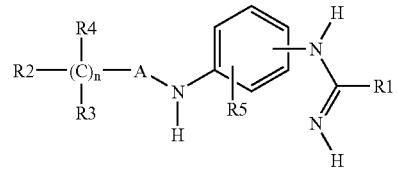

(I)

| Compound | $R_1$ | $R^2$ | $R^3$ | n | A | Crude formula | M.P. (crystallisation solvent)$^d$ | TLC ($R_f$)$^e$ |
|---|---|---|---|---|---|---|---|---|
| I-1 | $CH_3$ | $CH_3$ | — | 0 | NH—CS | $C_{10}H_{14}N_4S$ | 186.2–187.8 | 0.50 |
| I-2 | $CH_3$ | $CH_3$ | H | 2 | NH—CS | $C_{12}H_{18}N_4S$ | 188.1–189.1 (A) | 0.70 |
| I-3 | $CH_3$ | $CH_3$ | H | 3 | NH—CS | $C_{13}H_{20}N_4S$ | 182.3–183.1 (A) | 0.72 |
| I-4 | $CH_3$ | $CH_3$ | H | 4 | NH—CS | $C_{14}H_{22}N_4S$ | 190.7–191.4 (A) | 0.71 |
| I-5 | $CH_3$ | $CH_3$ | H | 5 | NH—CS | $C_{15}H_{24}N_4S$ | 177.6–178.0 | 0.80 |
| I-6 | $CH_3$ | $CH_3$ | H | 6 | NH—CS | $C_{16}H_{26}N_4S$ | 177.8–178.4 | 0.80 |
| I-7 | $CH_3$ | Isopropyl | H | 2 | NH—CS | $C_{14}H_{22}N_4S$ | 177.7–179.1 (A) | 0.58 |
| I-8 | $CH_3$ | $CH_3$ | $CH_3$ | 1 | NH—CS | $C_{12}H_{18}N_4S$ | 163.0–163.9 (A) | 0.58 |
| I-9 | $CH_3$ | Ethyl | $CH_3$ | 1 | NH—CS | $C_{14}H_{22}N_4S$ | 145.7–147.4 (B) | 0.61 |
| I-10 | $CH_3$ | $CH_3$—O | H | 3 | NH—CS | $C_{13}H_{24}N_4OS$ | 146.9–149.6 (B) | 0.54 |
| I-11 | $CH_3$ | Cyclohexyl | — | 0 | NH—CS | $C_{15}H_{22}N_4S$ | 171.3–171.6 (A) | 0.60 |
| I-12 | Ethyl | Cyclohexyl | — | 0 | NH—CS | $C_{16}H_{24}N_4S$ | 155.0–156.0 | 0.66 |
| I-13 | $CH_3$ | Phenyl | H | 0 | NH—CS | $C_{15}H_{16}N_4S$ | 118.7–120.5 | 0.70 |
| I-14 | $CH_3$ | Phenyl | H | 2 | NH—CS | $C_{17}H_{20}N_4S$ | 186.6–188 | 0.63 |

TABLE 2-continued

Compounds of formula (I)

(I)

$$R2-(C)_n-A-N(H)-\text{[phenyl with R5]}-N(H)-C(R1)=N-H$$
with R4, R3 on the carbon

| Compound | $R_1$ | $R^2$ | $R^3$ | n | A | Crude formula | M.P. (crystallisation solvent)$^d$ | TLC $(R_f)^e$ |
|---|---|---|---|---|---|---|---|---|
| I-15 | $CH_3$ | Phenyl | H | 3 | NH—CS | $C_{18}H_{22}N_4S$ | 146.6–148.0 (B) | 0.60 |
| I-16 | $CH_3$ | 4-F-Phenyl | H | 2 | NH—CS | $C_{17}H_{19}FN_4S$ | 179.1–181.6 | 0.57 |
| I-17 | $CH_3$ | 4-Cl-Phenyl | H | 2 | NH—CS | $C_{17}H_{19}ClN_4S$ | 174.0–176.0 (A) | 0.60 |
| I-18 | $CH_3$ | 2,6-diF-Phenyl | H | 2 | NH—CS | $C_{17}H_{18}F_2N_4S$ | 158.8–160.4 | 0.58 |
| I-19 | $CH_3$ | 2-Piridyl | H | 1 | NH—CS | $C_{15}H_{17}N_5S$ | 159.0–161.0 (A) | 0.48 |
| I-20 | $CH_3$ | 2-Piridyl | H | 2 | NH—CS | $C_{16}H_{19}N_5S$ | 171.5–173.0 (A) | 0.42 |
| I-21 | $CH_3$ | 5-$CH_3$-2-Thiazolyl | — | 0 | NH—CS | $C_{13}H_{15}N_5S_2$ | 107.8–110.1 | 0.45 |
| I-22 | $CH_3$ | $CH_3$ | H | 4 | NH—CS | $C_{16}H_{26}N_4S$ | 118–121.7 (B) | 0.61 |
| I-23 | $CH_3$ | $CH_3$ | H | 4 | CO | $C_{14}H_{21}N_3O$ | 160.4–161.6 | 0.60 |
| I-24 | $CH_3$ | Cyclohexyl | — | 0 | CO | $C_{15}H_{21}N_3O$ | 194.6–195.8 (B) | 0.60 |
| I-25 | $CH_3$ | 1-Adamantyl | — | 0 | CO | $C_{19}H_{25}N_3O$ | 224.4–224.7 | 0.61 |
| I-26 | $CH_3$ | 2-Indolyl | — | 0 | CO | $C_{17}H_{16}N_4O$ | 192.0–193.5 | 0.61 |
| I-27 | $CH_3$ | 3-Indolyl | H | 1 | CO | $C_{18}H_{18}N_4O$ | 159.0–160.0 | 0.51 |
| I-28 | $CH_3$ | 1-$CH_3$-2-Indolyl | — | 0 | CO | $C_{18}H_{18}N_4O$ | 195.5–196.5 | 0.68 |
| I-29 | $CH_3$ | Cyclohexyl | — | 0 | NH—CO | $C_{15}H_{22}N_4O$ | 220.2–224.6 | 0.50 |
| I-30 | $NH_2$ | Cyclohexyl | — | 0 | NH—CS | $C_{14}H_{21}N_5S$ | 176.5–179.4 | 0.71 |
| I-31 | $NO_2$—NH | Cyclohexyl | — | 0 | NH—CS | $C_{14}H_{20}N_6O_2S$ | 213.9–215.2 | 0.95 |
| I-32 | $CH_3$ | Cyclohexyl | — | 0 | NH—CS | $C_{15}H_{22}N_4S$ | 171.4–173.2 | 0.66 |

Note:
a) In all of the compounds given by example, $R_4$ is H, with the exception of compound I-9 in which $R_4$ is $CH_3$.
b) In all of the compounds given by way of example, the amino group is in the para position relative to the "NH-A" group, with the exception of compound I-32 in which the amino group is in the meta position relative to the "NH-A" group.
c) In all of the compounds given by way of example, $R_5$ is H, except for compound I-22 in which $R_5$ is 2,5-dimethyl.
$^d$Crystallisation solvent: A (acetonitrile); B (toluene).
$^e$Eluent: butanol/acetic acid/water (5/2/2) (v/v).

PHARMACOLOGICAL ACTIVITY a) The activity in inhibiting the formation of NO, measured as $NO_2^-$ (nitrites), $PGE_2$, and neutral protease, was investigated in vitro on culture broths of rabbit joint chondrocytes stimulated by cytokine IL-1β (1 ng/ml) for 48 hours. For the preparation of the chondrocytes, the method described by Berenbaum et al [FEBS Letters 340, 51–55 (1994)] was followed. Briefly, fragments of cartilage removed under sterile conditions from the heads of rabbit shoulder, hip and knee joints were chopped finely and digested at 37° C. by hyaluronidase, trypsin and collagenase solutions, giving rise, after filtration on sterile gauze and centrifuging at 600×g and suitable dilution with 10% DMEM-FCS, to a concentration of approximately 1×10$^5$ cells per well. The cells were kept in these conditions until confluence (about 15 days), the broth being changed every 3 days. At this point, the products under test, dissolved in the medium, were added to each test sample and, after 20 minutes, 350 μl IL-1β was added in order to have a final concentration of 1 ng/ml. The duration of the stimulation was 48 hours at 37° C. (incubation air-$CO_2$ 7%). Measurement of the nitrites, as described by Green et al. [Anal. Biochem. 126, 131–138 (1982)], and of the $PGE_2$s by RIA measurement, was then performed on the cell supernatant fluid. The measurement of the neutral proteases was performed in the cell supernatant fluid containing the p-aminophenyl mercury acetate (APMA) activator with the use of azocoll as the substrate and with incubation at 37° C. for 17 h as described by Chavira et al. [Anal. Biochem. 136, 446–450 (1984)]. In order to evaluate the direct inhibitory effect of the compounds under test on the hydrolytic activity of the cell supernatant fluid, they were added to the supernatant fluid containing the proteases induced by IL-1β and already activated by AMPA.

The results obtained are shown in Table 3, in which the $IC_{50}$, that is, the concentration (micromolar) of antagonist which can inhibit the formation of nitrites, $PGE_2$s, and neutral proteases, respectively, by 50% relative to the control group, that is, to the cells stimulated with IL-1β but without the addition of antagonists, is given for some of the compounds of the invention already given by way of example in Table 2.

TABLE 3

Compounds of formula (I)

$$R2-\underset{R3}{\overset{R4}{(C)_n}}-A-\underset{H}{N}-\text{[phenyl with R5]}-\underset{H}{N}-\underset{\underset{H}{N}}{\overset{\|}{C}}-R1 \quad (I)$$

| Compound | R$_1$ | R$_2$ | R$_3$ | n | A | Rabbit joint chondrocytes IC$_{50}$ (× 10$^{-6}$M) NO | PGE2 | MP |
|---|---|---|---|---|---|---|---|---|
| I-1 | CH$_3$ | CH$_3$ | — | 0 | NH—CS | IN | IN | 30 |
| I-2 | CH$_3$ | CH$_3$ | H | 2 | NH—CS | IN | IN | 30 |
| I-3 | CH$_3$ | CH$_3$ | H | 3 | NH—CS | 190 | 250 | 13.3 |
| I-4 | CH$_3$ | CH$_3$ | H | 4 | NH—CS | 6.6 | 3.3 | 6.6 |
| I-5 | CH$_3$ | CH$_3$ | H | 5 | NH—CS | 10.0 | 10.0 | 3.3 |
| I-6 | CH$_3$ | CH$_3$ | H | 6 | NH—CS | 30.0 | 20.0 | 20.0 |
| I-7 | CH$_3$ | Isopropyl | H | 2 | NH—CS | 3.3 | 6.6 | 13.3 |
| I-8 | CH$_3$ | CH$_3$ | CH$_3$ | 1 | NH—CS | 30.0 | 3.3 | 3.3 |
| I-9 | CH$_3$ | C$_2$H$_5$ | CH$_3$ | 1 | NH—CS | 10.0 | 10.0 | 6.6 |
| I-10 | CH$_3$ | CH$_3$—O | H | 3 | NH—CS | 50.0 | 50.0 | 6.6 |
| I-11 | CH$_3$ | Cyclohexyl | — | 0 | NH—CS | 110 | 16.6 | 30 |
| I-12 | Ethyl | Cyclohexyl | — | 0 | NH—CS | IN | 13.3 | 100 |
| I-13 | CH$_3$ | Phenyl | H | 0 | NH—CS | 100 | 10 | 6.6 |
| I-14 | CH$_3$ | Phenyl | H | 2 | NH—CS | 100 | 33 | 6.6 |
| I-15 | CH$_3$ | Phenyl | H | 3 | NH—CS | 33 | 16.6 | 6.6 |
| I-16 | CH$_3$ | 4-F-Phenyl | H | 2 | NH—CS | 13.3 | 26.6 | 6.6 |
| I-17 | CH$_3$ | 4-Cl-Phenyl | H | 2 | NH—CS | 10.0 | 10 | 10 |
| I-18 | CH$_3$ | 2,6-diF-Phenyl | H | 2 | NH—CS | IN | 6.6 | 6.6 |
| I-19 | CH$_3$ | 2-Piridyl | H | 1 | NH—CS | 300 | IN | 13.3 |
| I-20 | CH$_3$ | 2-Piridyl | H | 2 | NH—CS | 16.6 | 16.6 | 6.6 |
| I-21 | CH$_3$ | 5-CH$_3$-2-Thiazolyl | — | 0 | NH—CS | 66.6 | IN | IN |
| I-22 | CH$_3$ | CH$_3$ | H | 4 | NH—CS | 16.6 | 10.0 | 20.0 |
| I-23 | CH$_3$ | CH$_3$ | H | 4 | CO | 100 | IN | IN |
| I-24 | CH$_3$ | Cyclohexyl | — | 0 | CO | 33.3 | 33.3 | IN |
| I-25 | CH$_3$ | 1-Adamantyl | — | 0 | CO | IN | 16.6 | IN |
| I-26 | CH$_3$ | 2-Indolyl | — | 0 | CO | 300 | IN | IN |
| I-27 | CH$_3$ | 3-Indolyl | H | 1 | CO | 10 | IN | IN |
| I-28 | CH$_3$ | 1-CH$_3$-2-Indolyl | — | 0 | CO | IN | 100 | IN |
| I-29 | CH$_3$ | Cyclohexyl | — | 0 | NH—CO | 25.0 | 6.6 | 25.0 |
| I-30 | NH$_2$ | Cyclohexyl | — | 0 | NH—CS | 6.6 | 10 | 13.3 |
| I-31 | NO$_2$—NH | Cyclohexyl | — | 0 | NH—CS | 46.6 | 30 | 6.6 |
| I-32 | CH$_3$ | Cyclohexyl | — | 0 | NH—CS | 300 | 300 | IN |
| L-NAME | — | — | — | — | — | IN | 3 (mM) | IN |

Note:
a) for the structural identification, see Notes a, b and c of Table 2
b) NO determined as nitrites
c) MR: metalloproteases It can be seen from the data given in Table 3 that some of the compounds which were tested and which are subjects of the invention have a potent inhibitory effect, at micromolar level, on the production of nitrites, PGE$_2$s and metalloproteases induced by IL-1β cytokine in rabbit chondrocyte cultures. The best compounds were those in which R$_1$ was CH$_3$, R$_3$ and R$_4$ were H, R$_2$ was CH$_3$ if n was 4 or 5, isopropyl if n was 2, or the 2,6-difluoro-phenyl group if n was 2, and in which A was NH—CS (compounds I-4, I-5, I-7 and I-18, respectively). Compound I-31 in which R$_1$ was the NH—NO$_2$ group, R$_2$ was cyclohexyl, and A was the NH—CS group was also very active. It is interesting to note that the inhibitory activity on the metalloproteases was expressed solely by the compounds in which A was the NH—CS group. It should also be noted that the reference NO-synthase inhibitor compound L-NAME generally had an activity about 30–100 times less potent than the best compounds of the invention, such as the compound I-4, and was completely inactive in inhibiting the metalloproteases.

b) Some of the compounds of the invention, such as compounds I-4, I-11 and I-31, were evaluated in vivo in a series of experimental extravasation models in which 5 μl of the preselected phlogogenic agent dissolved in physiological solution was injected intradermally into the ears of mice as described by Erdo et al., with slight modifications [Agents and Actions 39, 137–142 (1993)].

The products under test were administered orally 1 hour before the challenge and, 30 minutes before the challenge, the dye Evans Blu was injected intravenously in a dose of 100 mg/kg. The animals were killed at a time predetermined according to the test, 30 min.–2 hours after the challenge. The extravasation was evaluated by determining the quantity of dye present in the ear, extracted after homogenisation of the tissue in 2 ml of formamide and incubation at 50° C. for 2 hours. After centrifuging, the amount of dye was determined by measuring the absorption at 620 nm. The maximum % effect (% MPE) was calculated by the following formula:

$$\% \, MPE = \frac{(E_V - E_D)}{E_V - E_B} \times 100$$

in which $E_V$ is the mean absorption observed in the group of animals treated solely with the phlogogenic agent, $E_D$ is the group treated with the phlogogenic agent and the drug, and $E_B$ is the base value, that is, the value for the animals injected with physiological solution alone.

The phlogogenic agents used were:

Arachidonic acid (dissolved in EtOH); (1 mg/mouse; killed+30 min); histamine (3 nmoli/mouse; killed+30 min); PAF (30 pmoli/mouse; killed+60 min); Zymosan (10 μg/mouse; killed+120 min); bradykinin (0.6 nmoli/mouse; killed+30 min).

The results obtained with Compound I-4 are summarised in Table 4.

TABLE 4

Activity of Compound I-4 on extravasation induced by algogenic agents in the ears of mice
% inhibition effects

| Dose mg/kg (OS) | Arachidonic Acid | Histamine | PAF | Zymosan | Bradykinin |
|---|---|---|---|---|---|
| Duration | 30 min | 30 min | 1 h | 2 h | 30 min |
| 2.5 mg/kg | — | — | 41.9 | 40.0 | — |
| 5 mg/kg | 37.8 | 17.8 | 49.9 | 66.6 | 30.1 |
| 10 mg/kg | 40.0 | 27.7 | 55.1 | 65.8 | 30.7 |
| 20 mg/kg | 52.6 | 38.8 | 56.4 | 83.9 | 49.1 |
| 40 mg/kg | 55.5 | 52.5 | 66.2 | 89.8 | 51.3 |
| 80 mg/kg | — | — | — | 95.5 | — |

Compound I-4 was found to be particularly effective in extravasation induced by Zymosan ($ED_{50}$ 3.1 mg/kg); however, in the other extravasation models investigated, a dose of only 5 mg/kg also produced a mean inhibitory effect of approximately 35%. A non-selective NO-synthase inhibitor, N-nitro-L-arginine methyl ester (L-NAME), a $COX_1$ inhibitor (Piroxicam) and a $COX_2$ inhibitor (Nimesulide) were used as comparison drugs.

The results obtained are given in Table 5 below.

TABLE 5

Inhibition of extravasation in the ears of mice induced by algogenic agents
($ED_{50}$ mg/kg OS)

| | AA | Histamine | PAF | Zymosan | Bradykinin |
|---|---|---|---|---|---|
| Compound I-4 | 20.5 | 37.0 | 6.1 | 3.1 | 32.6 |
| Compound I-31 | 30.5 | — | 10.8 | 10.5 | — |
| L-NAME | 55.1 | 36.4 | 40.0 | IN (>100) | 39.4 |
| Piroxicam | — | — | 21.2 | 6.1 | — |
| Nimesulide | 41.0 | — | IN (>40) | — | — |

Note:
AA = Arachidonic acid
—: not tested

In general, Compound I-4 was the most active of the compounds investigated. In fact, of the reference compounds, L-NAME was approximately as active as Compound I-4 in extravasation induced by histamine and bradykinin but was two times less active in extravasation by AA, much less active in antagonising PAF, and completely inactive in extravasation induced by Zymosan.

Piroxicam was 2–3 times less active than Compound I-4 in the models in which PAF and Zymosan were used, and Nimesulide was less active (2 times) in antagonising AA and was inactive in antagonising PAF. Compound I-31 had an activity profile similar to that of compound I-4 but was generally 2–3 times less active.

c) The immunosuppressive activity of Compound I-4 was evaluated in an in vivo test in the rat, in which a lipopolysaccharide (LPS) of bacterial origin, injected i.p. at a dose of 6 mg/kg, induced a shock characterised by urgent diarrhoea accompanied by a large increase in the plasma TNFα concentration.

Blood was taken from the animals which were killed 90 minutes after the challenge and the concentration of TNFα in the plasma was determined by Elisa (Amersham Kit cod. RPN2734). The results thus obtained are given in Table 6.

TABLE 6

Effects of Compound I-4 on plasma TNFα concentration in rats after stimulation with LPS (6 mg/kg/I.P.)

| | TNFα (ng/ml ± SD) | | Inhibition (%) |
|---|---|---|---|
| Control (SHAM) | <1 | (n = 4) | — |
| Control LPS | 61 ± 13.4 | (n = 8) | — |
| Compound I-4 (50 μg/kg ICV) + LPS | 2.3 ± 1.2 | (n = 6) | 96.2 |
| Compound I-4 (10 mg/kg IV) + LPS | 12.9 ± 7.2 | (n = 6) | 78.9 |
| Compound I-4 (20 mg/kg OS) + LPS | 30.6 ± 1.0 | (n = 6) | 49.8 |

It is clear from the data given above that compound I-4 is very active in inhibiting the increase in plasma TNFα in the course of endotoxic shock induced by LPS. For example, the oral dose of 20 mg/kg inhibited the effect of the LPS by about 50%.

d) Intestinal anti-inflammatory Activity.

TNFα is a cytokine implicated in the pathogenesis of a variety of immunology-based inflammatory diseases, amongst which is inflammation of the intestine. It has been shown [Bertrand et al. Br. J. Pharmacol. 124, 1385–1394 (1998)] that inducing an overproduction of TNFα, induced by $COX_1$-type anti-inflammatory drugs, brings about activation of the neutrophiles and an increase in the production of nitrites due to the activation of the tissue iNOS, which together contribute to the toxic-ulcerative effects on the intestinal mucosa.

The combined capability of some of the compounds of the invention to inhibit both iNOS and the synthesis of TNFα has led to their activity being checked in an experimental model of colitis caused by a chemical hapten, trinitrobenzenesulphonic acid (TNBS), which can bind to the tissue proteins and stimulate cell-mediated immunity. The intrarectal administration of TNBS in association with ethanol causes acute inflammation characterised by extensive ulceration and necrosis.

A distal colitis was therefore induced in the rat by intrarectal instillation of TNBS (40 mg/kg) dissolved in 50% ethanol (0.5 ml/rat). The drugs were administered orally twice a day on days −2; −1; 0; +1 and the animals were killed 48 hours after the administration of TNBS.

The parameters examined were: total weight of the colon (g), macroscopic tissue damage "score", measurement of the tissue myeloperoxidase (MPO) activity, which is a marker of the infiltration of the neutrophiles, and measurement of the iNOS activity (pmoles/g tissue/min.).

The macroscopic score (MDS) was taken on about 10 cm of colon in accordance with the following arbitrary scale:

| | |
|---|---|
| 0 | No damage |
| 1 | Hyperaemia (no ulcers) |
| 2 | 1 small ulcer or erosion |
| 3 | 1 ulcer with inflammation |
| 4 | Two ulceration sites |
| 5 | More than two ulceration sites or 1 ulcer > 1 cm |
| 6–10 | If the damage was > 2 cm, the score was increased by 1 for each cm |

The tissue MPO measurement was performed according to Velgara et al., JPET 1994. The measurement of the tissue nitrites was performed by applying the method described above for the chondrocytes to the supernatant fluid of the tissue homogenate.

Compound I-4, administered in doses of 5, 10 and 20 mg/kg, and compound I-11 were examined, by administering them orally, in comparison with sulphasalazine (250 mg/kg) and 5-aminosalicylic acid (5-ASA) (100 mg/kg), 2 drugs which are widely used in the treatment of ulcerative colitis.

The results thus obtained are given in the following table.

TABLE 7

Effects of compound I-4, I-11, sulphasalazine and 5-ASA on colitis induced by TNBS in rats

| Treatment groups [mg/kg; number (n)] | Weight of the colon (g) | Macroscopic damage (MDS) | Myeloperoxidase activity (UMPO/g/min) | iNOS activity (pmoles/g/min) |
|---|---|---|---|---|
| Control (SHAM) (n = 6) | 1.5 ± 0.2 | — | 0.9 ± 0.3 | 6.6 ± 4.4 |
| Control (TNBS) (n = 8) | 2.4 ± 0.3 | 7.4 ± 1.4 | 7.7 ± 1.1 | 190.9 ± 98.6 |
| I-4 (5 mg/kg; n = 8) | 2.2 ± 0.2 | 5.0 ± 0.9 | 5.5 ± 1.4 | 131.7 ± 91.9 |
| I-4 (10 mg/kg; n = 8) | 2.1 ± 0.3 | 4.4 ± 0.8(*) | 5.0 ± 1.7(*) | 98.6 ± 60.0 |
| I-4 (20 mg/kg; n = 8) | 2.0 ± 0.2(*) | 3.5 ± 0.8(*) | 5.1 ± 1.2(*) | 61.5 ± 31.4(*) |
| I-11 (20 mg/kg; n = 7) | 2.2 ± 0.3 | 4.3 ± 0.9(*) | 6.5 ± 1.8 | 90.6 ± 45.6(*) |
| 5-ASA (100 mg/kg; n = 7) | 2.4 ± 0.4 | 6.9 ± 1.1 | 7.9 ± 2.3 | 167.3 ± 106.5 |
| Sulphasalazine (250 mg/kg; n = 7) | 2.5 ± 0.3 | 6.0 ± 2.9 | 7.5 ± 5.5 | 100.8 ± 86.8 |

The values given are means ± Standard Deviation
(*)value significantly different from the TNBS control group (Duncan's test)

It is clear from the data given in the table that compound I-4 had a strong protective effect in the experimental model of colitis induced in the rat by TNBS. In fact I-4 reduces both macroscopic damage and all of the other inflammatory parameters taken into consideration in a dose-dependent and significant manner at medium and high dose (10 and 20 mg/kg). In particular, it reduces the increase in the weight of the colon induced by treatment with TNBS, reduces macroscopic damage by about 50% at doses of 10 and 20 mg/kg, and reduces the increase in tissue MPO activity and iNOS activity induced by TNBS by 40% and 50%, respectively, at the same doses. In contrast, of the two reference drugs selected, 5-ASA (100 mg/kg) was inactive on all of the parameters, and sulphasalazine was slightly active at the very high dose of 250 mg/kg and in a non-statistically significant manner solely on macroscopic damage (about 20% effect) and on iNOS activity (about 50% effect). The other compound of the invention which was tested (Compound I-11) was also active at the dose of 20 mg/kg although the effects in reducing damage, on the parameters of increase of the weight of the colon, and MPO activity were less clear than those of the compound I-4.

Finally, in an experimental model of colitis in the rat which imitates as closely as possible a pathological condition which can be correlated with ulcerative colitis in man [Morris et al. Gastroenterology 96, 795–803, (1989)] some of the compounds of the invention have a protective effect much greater, and at lower doses, than that of sulphasalazine which is a drug widely used in the treatment of ulcerative colitis and Crohn's disease.

What is claimed is:

1. A method of treating degenerative joint diseases selected from the group consisting of rheumatoid arthritis and osteoarthritis, comprising administering to a patient in need thereof, a therapeutically effective amount of a pharmaceutical composition comprising a compound represented by formula (I) as an active ingredient, or a pharmaceutically acceptable salt thereof

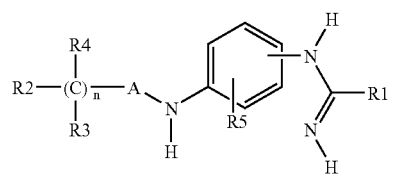

wherein

A is selected independently from a carboxamide group, a thiocarboxamide group, and a carbonyl group;

$R_1$ is selected from an alkyl group having from 1 to 3 carbon atoms and an amino group substituted with a nitro group or a methyl group;

$R_2$ is selected independently from hydrogen, an alkyl group having from 1 to 4 carbon atoms, a methoxy group, an ethoxy group, or a propoxy group, a mono-, bi- or tricyclic cycloalkane group having from 5 to 12 carbon atoms, an adamantyl group, and an aryl, naphthyl or heterocyclic group, unsubstituted or substituted with a methyl group, a methoxy group, a hydroxy group, an amino group or a halogen group;

$R_3$ and $R_4$ are selected independently from hydrogen and an alkyl group having from 1 to 3 carbon atoms;

$R_5$ represents one or two substituents independently selected from hydrogen and a methyl group, a methoxyl group and a hydroxyl group;

n is a whole number from 0 to 6; and an amidine group is in the para or meta position relative to the -A-NH— group.

2. A method of treating an inflammatory disease of the gastrointestinal tract selected from the group consisting of ulcerative colitis, irritable colon and Crohn's disease, comprising administering to a patient in need thereof, a therapeutically effective amount of a pharmaceutical composition comprising a compound represented by formula (I) as an active ingredient, or a pharmaceutically-acceptable salt thereof

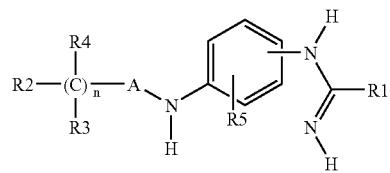

wherein

A is selected independently from a carboxamide group, a thiocarboxamide group, and a carbonyl group;

$R_1$ is selected from an alkyl group having from 1 to 3 carbon atoms and an amino group substituted with a nitro group or a methyl group;

$R_2$ is selected independently from hydrogen, an alkyl group having from 1 to 4 carbon atoms, a methoxy group, an ethoxy group, or a propoxy group, a mono-, bi- or tricyclic cycloalkane group having from 5 to 12 carbon atoms, an adamantyl group, and an aryl, naphthyl or heterocyclic group, unsubstituted or substituted with a methyl group, a methoxy group, a hydroxy group, an amino group or a halogen group;

$R_3$ and $R_4$ are selected independently from hydrogen and an alkyl group having from 1 to 3 carbon atoms;

$R_5$ represents one or two substituents independently selected from hydrogen and a methyl group, a methoxyl group and a hydroxyl group;

n is a whole number from 0 to 6; and an amidine group is in the para or meta position relative to the -A-NH— group.

* * * * *